United States Patent [19]
Tojo et al.

[11] Patent Number: 6,068,747
[45] Date of Patent: May 30, 2000

[54] SOLID ELECTROLYTE GAS SENSOR

[75] Inventors: Senta Tojo, Kariya; Makoto Saito, Okazaki; Keigo Mizutani, Okazaki; Hiroshi Mori, Ichinomiya; Yushi Fukuda, Chita-gun, all of Japan

[73] Assignees: Denso Corporation; Nippon Soken, Inc., both of Japan

[21] Appl. No.: 09/022,485

[22] Filed: Feb. 12, 1998

[30] Foreign Application Priority Data

Mar. 10, 1997 [JP] Japan .................................. 9-074481
Mar. 10, 1997 [JP] Japan .................................. 9-074482

[51] Int. Cl.[7] .............................................. G01N 27/407
[52] U.S. Cl. ........................ 204/425; 204/424; 204/426; 205/781; 205/784.5

[56] References Cited

U.S. PATENT DOCUMENTS

| | | | |
|---|---|---|---|
| 4,770,760 | 9/1988 | Noda et al. ............................. | 204/425 |
| 5,120,420 | 6/1992 | Nankai et al. .......................... | 204/403 |
| 5,126,034 | 6/1992 | Carter et al. ........................... | 204/403 |
| 5,145,566 | 9/1992 | Logothetis et al. .................... | 204/425 |
| 5,397,442 | 3/1995 | Wachsman ............................. | 204/425 |
| 5,493,896 | 2/1996 | Riegel et al. ........................... | 73/23.31 |
| 5,672,811 | 9/1997 | Kato et al. .............................. | 204/425 |
| 5,763,763 | 6/1998 | Kato ........................................ | 204/426 |

FOREIGN PATENT DOCUMENTS

| | | |
|---|---|---|
| 0 678740 A1 | 10/1995 | European Pat. Off. . |
| 0 731351 A2 | 9/1996 | European Pat. Off. . |
| A-64-39545 | 2/1989 | Japan . |
| A-4-359143 | 12/1992 | Japan . |
| A-4-359144 | 12/1992 | Japan . |
| A-4-359145 | 12/1992 | Japan . |
| A-5-322844 | 12/1993 | Japan . |
| A-8-29387 | 2/1996 | Japan . |

OTHER PUBLICATIONS

SAE 960334.
SAE 970858.

*Primary Examiner*—T. Tung
*Attorney, Agent, or Firm*—Nixon & Vanderhye PC

[57] ABSTRACT

A gas sensor using oxygen-ion-conductive solid electrolyte layers measures a concentration of a constituent gas such as NOx in a gas mixture such as an exhaust gas mixture of an internal combustion engine. The gas sensor includes a pair of oxygen pumping cells and a sensor cell. Before the constituent gas concentration is measured by the sensor cell, oxygen gas contained in the gas mixture has to be purged because the oxygen gas adversely affects the measurement of the constituent gas concentration. Two pumping cells disposed to face a chamber, into which the gas mixture is introduced, pump out the oxygen gas contained in the gas mixture so that the oxygen concentration is reduced substantially zero. Then, the gas mixture is diffused to the sensor cell where the constituent gas concentration is measured without the adverse influence of the oxygen gas. A marginal ion current which is proportional to the constituent gas concentration is measured by the sensor cell with a high accuracy and sensitivity.

29 Claims, 12 Drawing Sheets

LONGITUDINAL DIRECTION

SOLID ELECTROLYTE GAS SENSOR

CROSS-REFERENCE TO RELATED APPLICATIONS

This application is based upon and claims benefit of priority of Japanese Patent Applications No. Hei-9-74481 filed on Mar. 10, 1997, and No. Hei-9-74482 filed on Mar. 10, 1997, the contents of which are incorporated herein by reference.

BACKGROUND OF THE INVENTION

1. Field of the Invention

The present invention relates to a solid electrolyte gas sensor for detecting a concentration of a specific gas contained in a gas mixture, such as an NOx gas contained in an exhaust gas of an internal combustion engine.

2. Description of Related Art

Sensors for detecting an NOx concentration in an exhaust gas of an internal combustion engine, which are mounted on an exhaust gas passage, are known hitherto. Such sensors are used for controlling an internal combustion engine. An oxygen-ion-conductive solid electrolyte such as a stabilized zirconia is usually used for the sensor. The sensor is composed of a chamber, into which a gas mixture is introduced, and a sensor cell having a pair of electrodes disposed on both surfaces of an oxygen-ion-conductive solid electrolyte layer. One of the sensor cell electrodes which is made of an active material to reduce oxygen of the NOx gas in the mixture into oxygen ions is disposed to face the gas mixture chamber and the other electrode is disposed to face atmospheric air. The concentration of the NOx is measured based on an oxygen ion current flowing through the electrolyte which is proportional to the NOx concentration. However, since oxygen is contained in the gas mixture/such as the exhaust gas, oxygen in the gas mixture is also reduced to oxygen ions together with the oxygen of the NOx gas. Therefore, the gas sensor detects a total amount of oxygen ions of both oxygen in the gas mixture and oxygen in the NOx gas, and, accordingly, it is not possible to measure the ion current proportional only to the NOx concentration.

To eliminate the influence of the oxygen contained in the gas mixture, a gas sensor having an oxygen pumping cell for pumping out the oxygen from the mixture chamber has been proposed, for example, in JP-A-8-29387. The oxygen pumping cell is composed of a pair of electrodes disposed on both surfaces of an oxygen-ion-conductive electrolyte layer. One electrode made of a material which is inactive in reducing oxygen of the NOx gas is disposed to face the mixture chamber, and other electrode is exposed to atmospheric air. By imposing an electric voltage between the pair of electrodes, oxygen in the gas mixture at a vicinity of the pumping cell electrode is ionized and pumped out through the electrolyte. This pumping cell, however, has a drawback that only oxygen at the vicinity of the electrode is ionized and oxygen existing distant from the electrode is difficult to be ionized. Therefore, it is difficult to pump out the oxygen completely from the mixture chamber, and, accordingly, it is difficult to eliminate the influence of the oxygen in the gas mixture in the measurement of the NOx concentration. In other words, it is not possible to tell whether the NOx concentration has actually increased or the amount of oxygen in the gas mixture has increased even if the gas sensor indicates a higher value.

To cope with this problem, a gas sensor having an oxygen sensor cell for checking the oxygen concentration in the mixture chamber has been proposed in a SAE paper No. 960334. The oxygen sensor cell is composed of a pair of electrodes disposed on both surfaces of an oxygen-ion-conductive electrolyte layer. One of the electrodes is exposed to the mixture chamber and the other to atmospheric air. A voltage generated between the pair of electrodes in proportion to the oxygen concentration in the mixture chamber is fed back to the oxygen pumping cell to adjust a voltage to be supplied thereto, so that the oxygen concentration in the mixture chamber is kept at a constant level. This type of the gas sensor, however, has a drawback that the oxygen sensor cell occupying a certain space in the sensor is necessarily required. Accordingly, a space for the oxygen pumping cell is narrowed. Since a pumping capacity of the oxygen pumping cell is proportional to the area of its electrodes, the mount of oxygen pumped out by the pumping cell will decrease as the space for the pumping cell becomes smaller. As the pumping capacity decreases, an amount of the gas mixture introduced into the mixture chamber has to be decreased, resulting in a decrease of the ion current to be detected by the gas sensor. In other words, the sensitivity of the gas sensor is sacrificed. Further, since one electrode of the oxygen sensor has to be exposed to the atmospheric air, a structure of the gas sensor becomes complex.

Though the problems of conventional gas sensors are mentioned with reference to a gas sensor used for detecting the NOx concentration in the gas mixture, the same problems are common to gas sensors detecting other constituent gases such as SOx, $H_2O$, $CO_2$ or the like, as long as a constituent gas concentration is detected by a sensor cell in such a manner that the oxygen ion current resulting from reduction of the constituent gas is measured.

SUMMARY OF THE INVENTION

The present invention has been made in view of the above-mentioned problems, and an object of the present invention is to provide a solid electrolyte gas sensor for detecting a constituent gas concentration in a gas mixture with a high sensitivity and accuracy by eliminating the influence of oxygen contained in the gas mixture.

A pair of oxygen pumping cells are used in the gas sensor according to the present invention in order to pump out the oxygen gas contained in the gas mixture, so that the oxygen concentration is reduced to substantially zero. Each oxygen pumping cell is disposed to face the gas mixture introduced into a gas mixture chamber. Then, the gas mixture from which the oxygen has been purged is diffused to a sensor cell which measures a concentration of a constituent gas in the gas mixture. Thus, the adverse influence of the oxygen gas is eliminated, and the constituent gas concentration in the gas mixture can be measured with a high sensitivity and accuracy.

Each oxygen pumping cell is composed of an oxygen-ion-conductive solid electrolyte layer and a pair of electrodes disposed on both surfaces of the electrolyte layer. Two electrolyte layers are laminated on each other to form a gas mixture chamber into which the gas mixture is introduced, and one of the electrodes of each pumping cell is exposed to the mixture gas. When the constituent gas, the concentration of which is to be measured by the gas sensor is NOx gas, the electrodes of pumping cells exposed to the gas mixture are made of a material, such as an alloy of platinum and gold (Pt—Au), which is inactive in reducing oxygen of NOx in the gas mixture, and other electrodes are made of platinum (Pt) which is active.

The sensor cell for measuring the constituent gas concentration is composed of an oxygen-ion-conductive solid electrolyte layer and a pair of electrodes made of a material such as platinum (Pt) disposed on both surfaces of the electrolyte layer. The electrolyte layer carrying the pumping cell thereon may be commonly used as the electrolyte layer for the sensor cell. Preferably, two sensor cells are used in the gas sensor which are connected electrically in parallel to each other in order to obtain a higher output.

The electrolyte layers are made in a rectangular shape. The pumping cell and the sensor cell are aligned side by side either in the longitudinal direction of the electrolyte layer or in the direction perpendicular to the longitudinal direction. The diffusion distance of the gas mixture from the pumping cell to the sensor cell may be made shorter when both cells are aligned in the direction perpendicular to the longitudinal direction. In this case, both cells may be elongated along the longitudinal direction, and the gas mixture may be introduced into the gas mixture chamber from a plurality of inlet holes formed on the pumping cell.

A constant voltage is applied to both pumping cells which are connected electrically in parallel to each other, and another constant voltage may be applied to a sensor cell or a pair of sensor cells connected in parallel to each other. In case the voltage is applied to the sensor cell, a marginal ion current proportional to the constituent gas concentration is measured. It is also possible to detect a voltage representing the constituent gas concentration by the sensor cell without applying a voltage thereto.

In the diffusion path of the gas mixture from the pumping cell to the sensor cell, an oxygen sensor cell may be disposed for measuring the oxygen concentration in the gas mixture after the oxygen contained therein is pumped out by the pumping cells. The oxygen sensor monitors the residual oxygen concentration and feeds back this information to the pumping cells to control the oxygen concentration level in the gas mixture at a constant level. The electrolyte layers each carrying the oxygen pumping cell, the oxygen sensor cell and the sensor cell may be laminated in this order, and the diffusion path of the gas mixture may be made in the direction of lamination, i.e., in the thickness direction, thereby making the diffusion path shorter.

A heater layer may be laminated together with electrolyte layers carrying pumping cells and sensor cells to obtain a quicker response of the gas sensor.

Other objects and features of the present invention will become more readily apparent from a better understanding of the preferred embodiments described below with reference to the following drawings.

DETAILED DESCRIPTION OF THE PREFERRED EMBODIMENTS (First Embodiment)

A solid electrolyte gas sensor as a first embodiment according to the present invention will be described, referring to FIGS. 1 through 7. The first embodiment gas sensor is used for detecting an NOx concentration in a gas mixture in an exhaust pipe of an internal combustion engine. The gas sensor is installed in the exhaust pipe of the engine as shown in FIG. 5.

Figure 1:
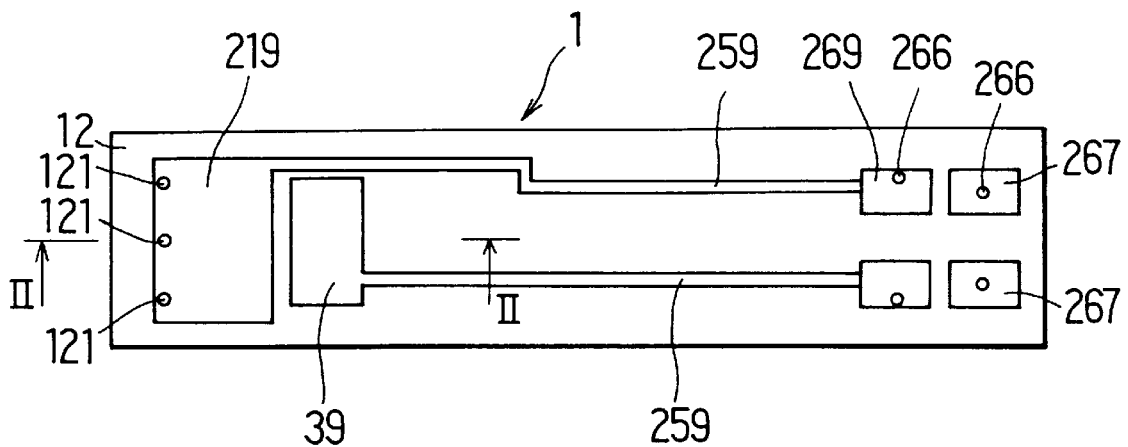
FIG. 1 is a top view showing a gas sensor as a first embodiment according to the present invention.
Figure 2:
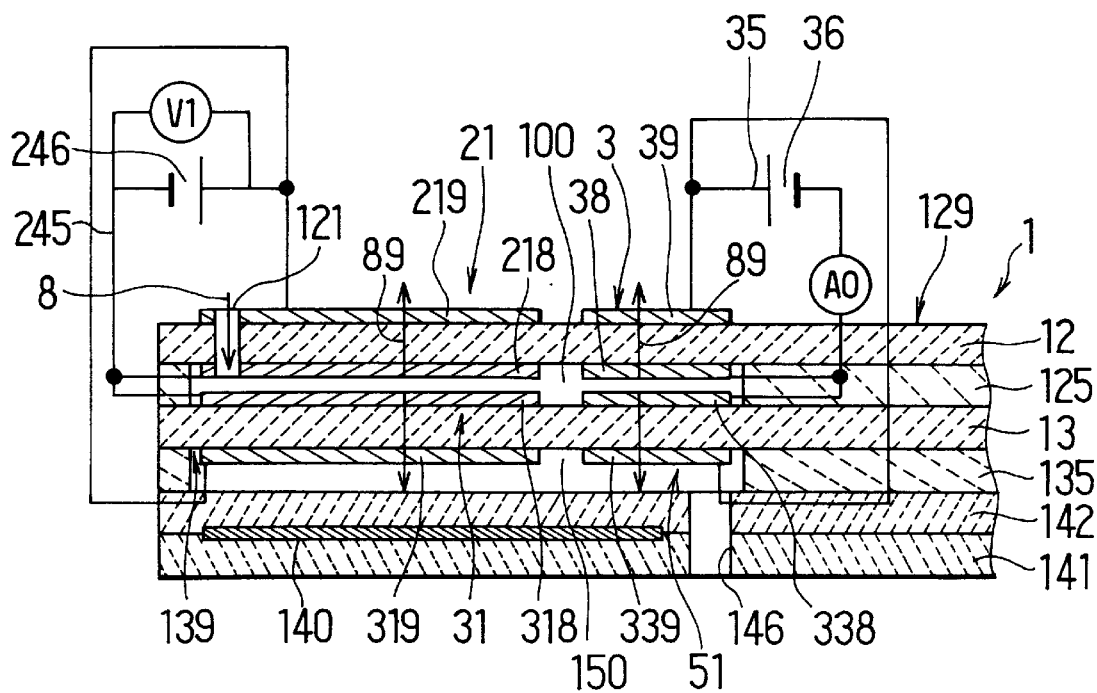
FIG. 2 is a cross-sectional view showing the gas sensor shown in FIG. 1, taken along a line II—II of FIG. 1.
Figure 3:
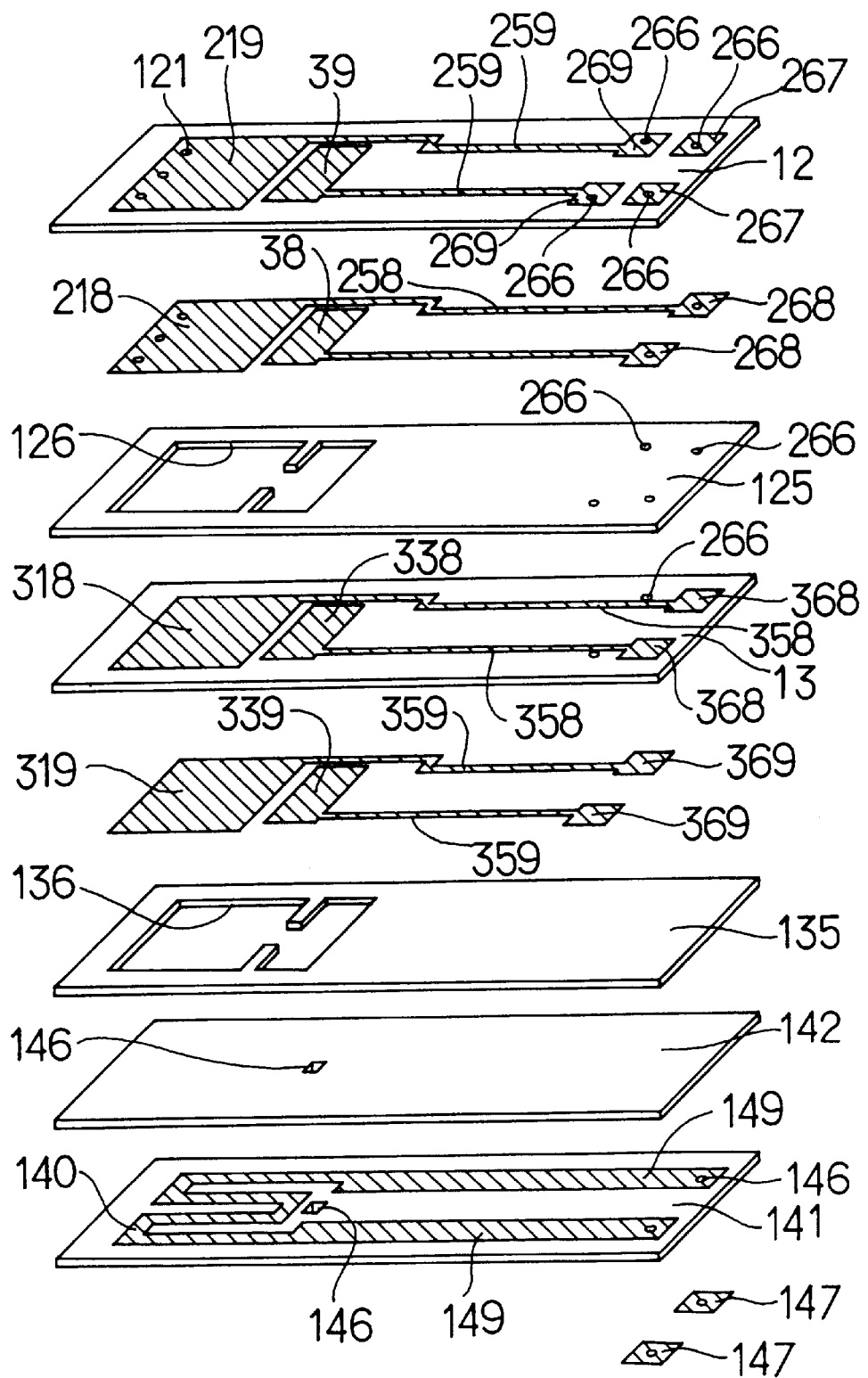
FIG. 3 is a perspective view showing each layer, separated from each other, used in the first embodiment.

As shown in FIGS. 1, 2 and 3, the gas sensor 1 includes two oxygen pumping cells (a first oxygen pumping cell 21 and a second oxygen pumping cell 31) and two sensor cells (a first sensor cell 3 and a second sensor cell 51). The gas mixture 8 is introduced into a gas mixture chamber 100 through an inlet hole (pin hole) 121. Oxygen gas 89 in the gas mixture chamber 100 is pumped out therefrom by operation of pumping cells 21 and 31. The gas mixture from which oxygen is eliminated is diffused to the sensor cell area, and the NOx concentration is measured by the sensor cells 3 and 51.

The first pumping cell 21 is composed of a first oxygen-ion-conductive electrolyte layer 12 and a pair of electrodes 218 and 219 disposed on both surfaces thereof. The second pumping cell 31 is composed of a second oxygen-ion-conductive electrolyte layer 13 and a pair of electrodes 318 and 319 disposed on both surfaces thereof. The first sensor cell 3 is composed of the first electrolyte layer 12 and a pair of electrodes 38 and 39 disposed on both surfaces thereof. The second sensor cell 51 is composed of the second electrolyte 13 and a pair of electrodes 338 and 339 disposed on both surfaces thereof. One electrode 218 of the first pumping cell 21 and one electrode 318 of the second pumping cell 31 face the gas mixture in the chamber 100. One electrode 38 of the first sensor cell 3 and one electrode 338 of the second sensor cell 51 face the gas mixture in the chamber 100. Both electrodes 218 and 318 facing the gas mixture are made of a material which is inactive in reducing oxygen of NOx into oxygen ions while all of the other electrodes 219, 319, 38, 39, 338 and 339 are made of a material which is active in reducing oxygen of NOx into oxygen ions. The first and the second oxygen pumping cells 21 and 31 are disposed to face each other in the gas mixture chamber 100. A constant voltage, for example, 0.8 V is imposed between the electrodes 218 and 219 of the first pumping cell 21 and between the electrodes 318 and 319 of the second pumping cell 31 from a power source 246. That is, two pumping cells 21 and 31 are connected in parallel with respect to the power source 246. By pumping out the oxygen in the gas mixture in the chamber 100 by operation of the pumping cells 21 and 31, the oxygen concentration therein is kept substantially zero (for example, less than 0.01 ppm). In the same manner, the first and the second sensor cells 3 and 51 are disposed to face each other in the gas mixture chamber 100. A constant voltage, for example, 0.5 V is imposed between the electrodes 38 and 39 of the first sensor cell 3 and between the electrodes 338 and 339 of the second sensor cell 51 from a power source 36. In other words, two sensor cells 3 and 51 are connected in parallel with respect to the power source 36.

The gas mixture chamber 100 is formed between the first electrolyte layer 12 and the second electrolyte layer 13, and underneath the second electrolyte layer 13 an air passage 150 is formed between the second electrolyte layer 13 and a heater layer 141 covered by a cover layer 142. The heater layer 141 with a heater film 140 disposed thereon heats the gas sensor 1. The air passage 150 is led to atmospheric air through a small hole 146. A spacer layer 125 is interposed between the first and the second electrolyte layers 12 and 13, and another spacer layer 135 is interposed between the second electrolyte layer 13 and the cover layer 142. The layers 125, 135, 141 and 142 are all made of alumina. The oxygen gas 89 is pumped out from the gas mixture chamber 100 by the first pumping cell 21 and the first sensor cell 3, while it is pumped out to the air passage 150 by the second pumping cell 31 and the second sensor cell 51.

Details of the sensor structure will be described, mainly referring to FIG. 3 in which each layer constituting the gas sensor 1 is separately shown from the top layer to the bottom layer. On the first electrolyte layer 12, the electrode 219 constituting the first pumping cell 21, the electrode 39 constituting the first sensor cell 3, and lead wires 259 and terminals 267 and 269 for connecting the electrodes in electric circuits 245 and 35 are disposed. Underneath the first electrolyte 12, there are the electrode 218 constituting the first pumping cell 21, the electrode 38 constituting the first sensor cell 3, and lead wires 258 and terminals 268 for their electric connections. The terminals 267 and 268 are electrically connected by through holes 266. The spacer layer 125 having a window 126 forming the gas mixture chamber 100 comes underneath the first electrolyte layer 12. Holes 266 thereon are for electrical connections. On the second electrolyte layer 13, there are disposed the electrode 318 constituting the second pumping cell 31, the electrode 338 constituting the second sensor cell 51, and lead wires 358 and terminals 368 for electrical connections. Underneath the second electrolyte 13, there are the electrode 319 constituting the second pumping cell 31, the electrode 339 constituting the second sensor cell 51, and lead wires 359 and terminals 369. The other spacer layer 135 having a window 136 forming the air passage 150 is disposed under the second electrolyte layer 13. Then comes the cover layer 142, having a small hole 146 for discharging the oxygen therethrough, for covering the heater layer 141. Underneath the cover layer 142, there is the heater layer 141 having a heater film 140 for heating the gas sensor, lead wires 149, and the small hole 146 for discharging the oxygen therethrough. Underneath the heater layer 141, terminals 147 for electrically connecting the heater film 140 via through holes 146 are disposed. The gas mixture is introduce to the mixture chamber 100 through inlet holes 121 (pin holes) formed at the left end of the electrodes 219 and 218 through the first electrolyte layer 12. The small hole 146 for discharging oxygen formed through the heater layer 141 is located at a position where it does not interfere with the heater film 140.

A voltmeter VI (shown in FIG. 2) for measuring the voltage of the pumping cells 21 and 31 connected in parallel is disposed in the circuit 245, and an ammeter A0 (shown in FIG. 2) for measuring the marginal ion current of the sensor cells 3 and 51 connected in parallel is disposed in the circuit 35.

The first and the second oxygen-ion-conductive electrolyte layers 12 and 13 are made of yttria-stabilized zirconia (YSZ), and the width, the length and the thickness thereof are 7 mm, 61 mm and 0.16 mm, respectively, in this particular embodiment. The spacer layers 125 and 135 are made of alumina, and the width, the length and the thickness thereof are 7 mm, 61 mm and 0.16 mm, respectively. The pumping cell electrodes 218 and 318 facing the gas mixture chamber 100 are made of a platinum-gold alloy (Pt—Au) containing 1 weight-percent of gold (Au). The other pumping cell electrodes 219 and 319 and all of the sensor cell electrodes 38, 39, 338 and 339 are made of platinum (Pt). The heater film 140 is made of platinum (Pt). The surface area of the pumping cell electrodes 218, 219, 318 and 319 is about 70 mm$^2$, and the surface area of the sensor cell electrodes 38, 39, 338 and 339 is about 12 mm$^2$ in this particular embodiment.

The gas sensor 1 is manufactured in the following processes. First, green sheets for the first and the second electrolyte layers 12 and 13, the spacer layers 125 and 135, the heater layer 141 and the cover layer 142 are made. Then, all of the electrodes, the lead wires, the terminals and the heater film are printed on respective green sheets. The green sheet layers are all laminated on each other in the order shown in FIG. 3, and baked under a pressure at a temperature of 1500° C.–1600° C. Thus, all the layers are formed in a single body as the gas sensor 1.

Figure 4:
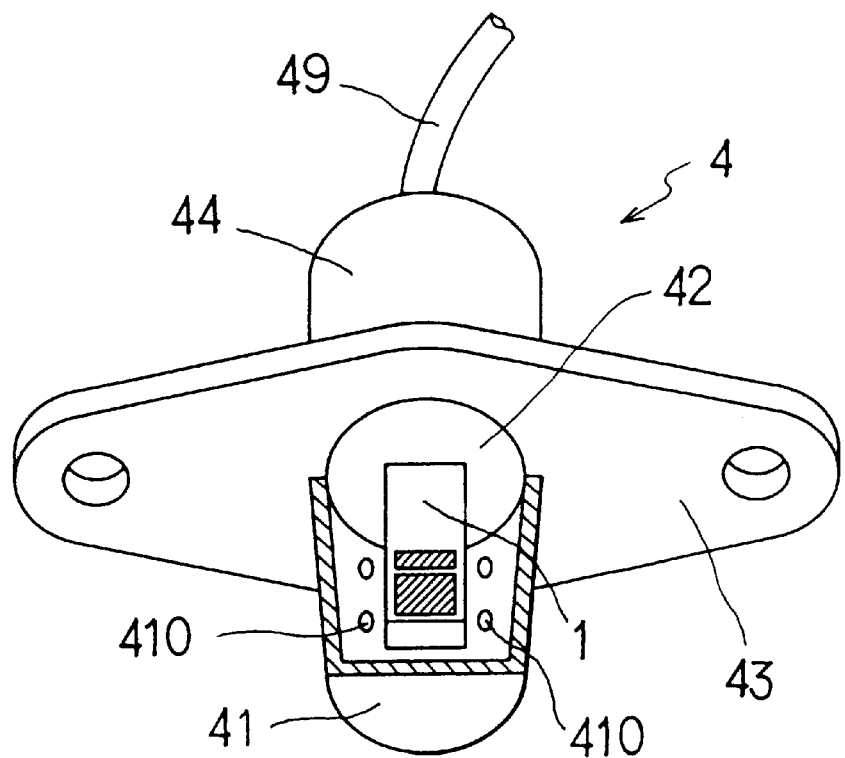
FIG. 4 is a perspective view, partly cross-sectioned, showing a gas sensor assembly to which the gas sensor according to the present invention is assembled.
Figure 5:
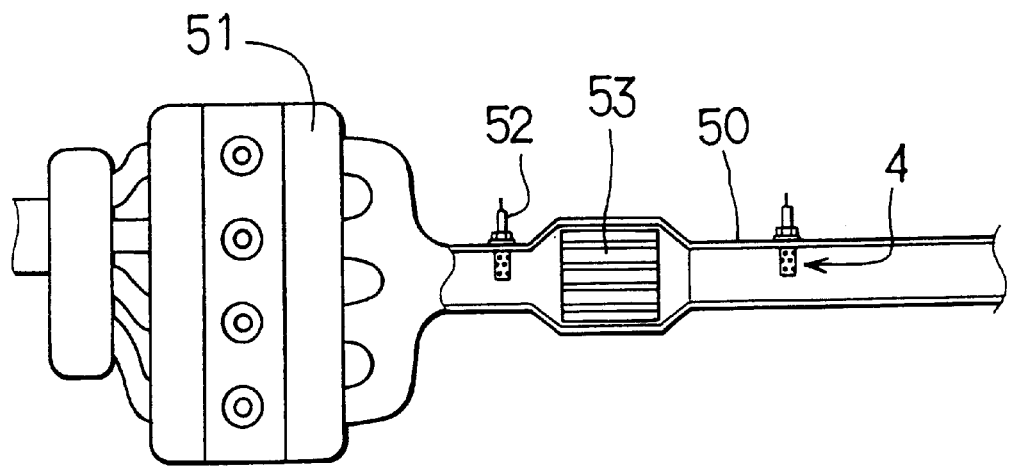
FIG. 5 is a drawing showing how the gas sensor is mounted on an exhaust pipe of an internal combustion engine.

The gas sensor 1 is assembled to a gas sensor assembly 4 shown in FIG. 4. The gas sensor assembly 4 includes a holder 42 for holding the gas sensor 1 thereon, a cover 41 for covering the gas sensor 1 and protecting the gas sensor 1 from the exhaust gas in the exhaust pipe of the engine, a housing 44 for containing therein lead wires 49 for electrical connections, and a flange 43 for mounting the gas sensor assembly 4 in the exhaust pipe. On the cover 41 holes 410 for introducing the gas mixture into the gas sensor 1 are formed. As shown in FIG. 5, the gas sensor assembly 4 is mounted on the exhaust pipe 50 at a downstream of a three-way catalyzer 53. At an upstream of the three-way catalyzer 53, an air-fuel ratio sensor 52 (A/F sensor) is mounted on the exhaust pipe 50. The exhaust gas from an engine 51 flows out through the exhaust pipe 50. A lean burn control of the engine 51 and a detection of deterioration of the three-way catalyzer 53 are performed based on signals from the gas sensor assembly 4 and the A/F sensor 52.

The NOx concentration in the gas mixture is detected by the solid electrolyte gas sensor 1 in the manner described below. The gas mixture 8 exhausted from the engine 51 flows through the three-way catalyzer 53 and reaches the gas sensor 1 in the exhaust pipe 50. The gas mixture 8 enters into the gas mixture chamber 100 through the inlet hole 121 as shown in FIG. 2. The oxygen gas 89 in the chamber 100 is pumped out by the oxygen pumping cells 21 and 31. A constant voltage (for example, 0.8 V) is imposed on both pumping cells 21 and 31, and thereby the oxygen concentration of the gas mixture in the chamber 100 is reduced to a level of substantially zero (for example, lower than 0.01 ppm). The gas mixture containing substantially no oxygen diffuses in the chamber 100 and reaches to the vicinity of the sensor electrodes 38 and 338. The oxygen of the NOx gas contained in the gas mixture is reduced into oxygen ions by contacting the sensor electrodes 38 and 338. As a constant voltage (for example, 0.5 V) is imposed on both of the first and the second sensor cells 3 and 51, an marginal ion current corresponding to the oxygen ion concentration, which is proportional to the NOx concentration, flows through the first and the second electrolyte 12 and 13 and is detected by the ammeter A0.

Figure 6A:
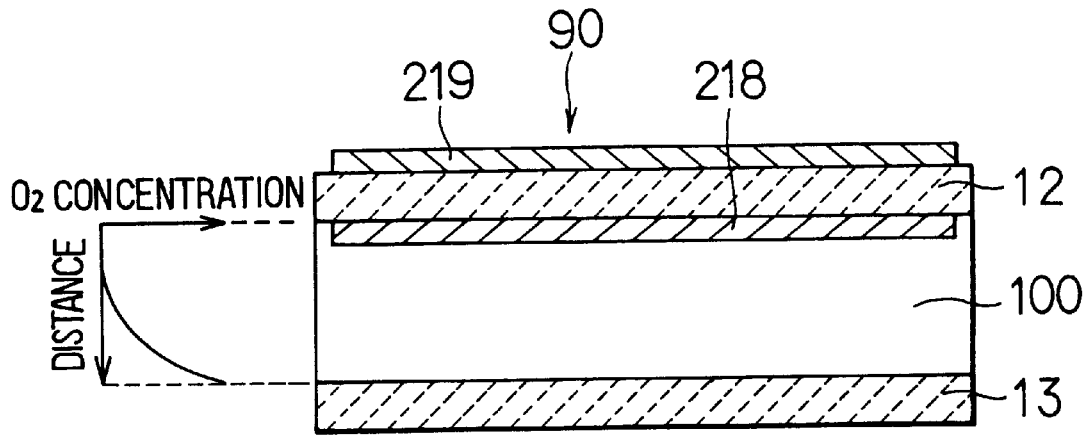
FIG. 6A is a cross-sectional view of a gas mixture chamber for explaining an oxygen concentration therein, in which only one oxygen pumping cell is used.
Figure 6B:
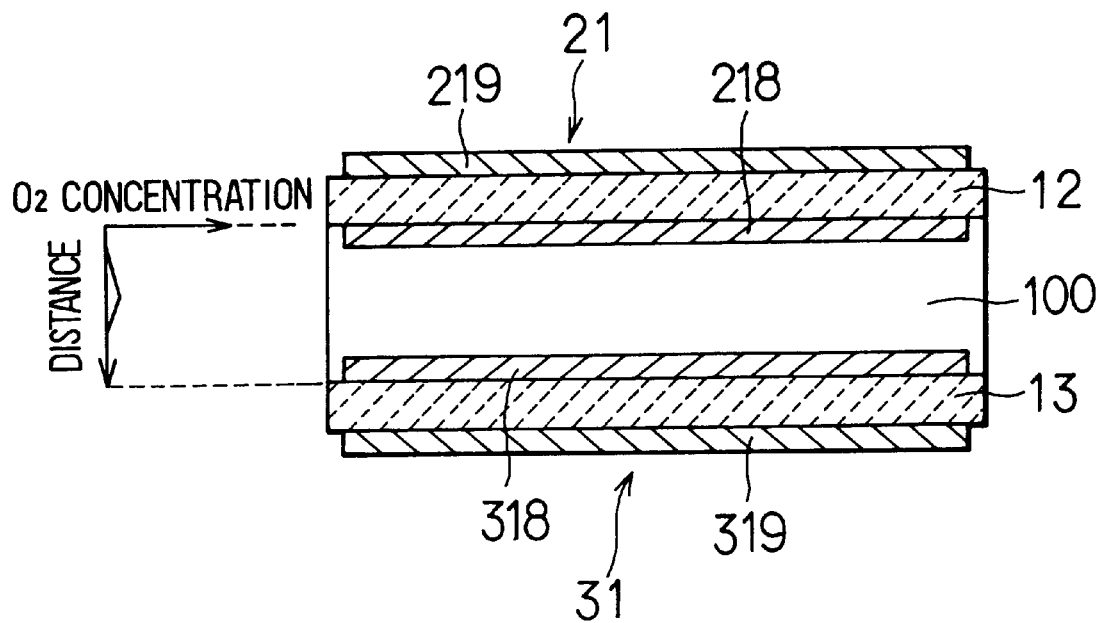
FIG. 6B is a cross-sectional view of the gas mixture chamber for explaining an oxygen concentration therein, in which two oxygen pumping cells are used.

In the process described above, it is important to reduce the oxygen concentration in the gas mixture to a level of substantially zero by the pumping cells 21 and 31 before the NOx concentration is measured by the sensor cells 3 and 51. If only one pumping cell 90 is provided to face the gas mixture in the chamber 100 as shown in FIG. 6A, only the oxygen in the gas mixture at a vicinity of the electrode 218 is ionized and pumped out through the first electrolyte 12 and the oxygen remote from the electrode 218 is not ionized nor discharged. Therefore, the oxygen concentration in the chamber 100 is not reduced uniformly and it shows a higher level at a vicinity of the second electrolyte 13, as shown by a graph at the left side of FIG. 6A. When two pumping cells 21 and 31 are disposed to face the chamber 100 as in the embodiment according to the present invention as shown in FIG. 6B, the oxygen in the gas mixture at a bottom part of the chamber 100 is also pumped out by operation of the second pumping cell 31. Therefore, the oxygen in the gas mixture is pumped out almost completely. Also, the amount of the oxygen pumped out from the chamber 100 becomes large, and, accordingly, a higher amount of the gas mixture can be introduced in the chamber 100. This contributes greatly to improving the sensor sensitivity to the constituent gas to be measured (NOx gas in the present embodiment).

Figure 7A:
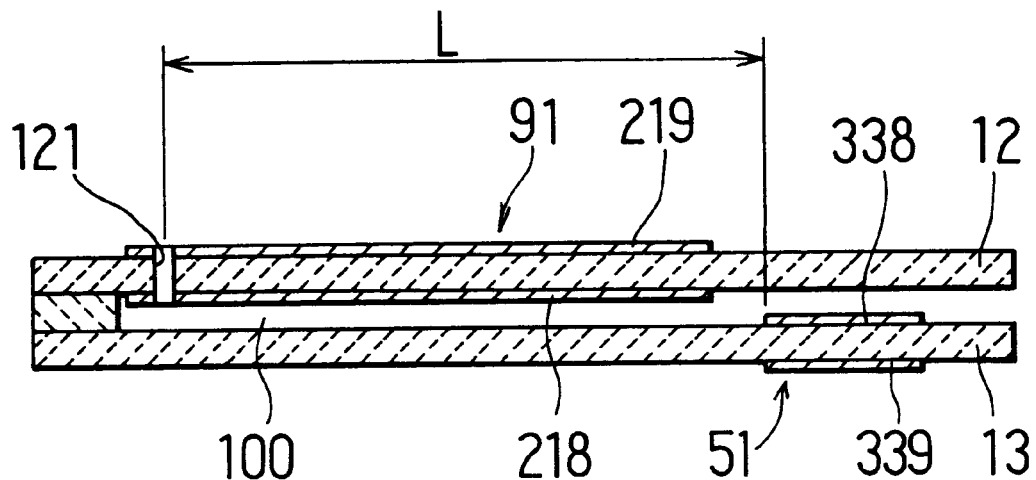
FIG. 7A is a cross-sectional view showing a gas sensor in which a single oxygen pumping cell having an enlarged area is used.
Figure 7B:
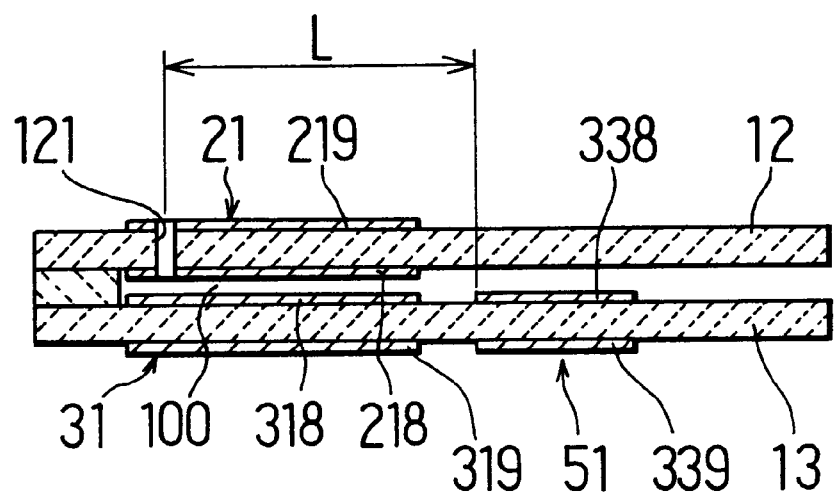
FIG. 7B is a cross-sectional view showing a gas sensor in which two oxygen pumping cells having a smaller area are used.

It may be possible to enlarge the surface area of a single pumping cell 91 to increase the amount of oxygen gas pumped out from the chamber 100, as shown in FIG. 7. However, in this case a diffusion length L (a distance from the gas mixture inlet port 121 to the sensor electrode 338) becomes long since a longitudinal length of the pumping cell electrode 218 also becomes long as the surface area of the electrode is enlarged. The longer the diffusion length L becomes, the smaller amount of the gas to be measured will reach the sensor cell. Accordingly, the sensitivity of the gas sensor becomes low. When two pumping cells 21 and 31 are disposed as in the embodiment of the present invention, a sufficiently large surface area of the pumping cell electrode can be provided without making the diffusion distance L longer, as shown in FIG. 7B. Further, since two sensor cells 3 and 51 are disposed to face each other in the chamber 100 in the present invention as shown in FIG. 2, the NOx concentration can be detected by cooperation of two sensor cells. Therefore, the sensor sensitivity is enhanced.

Since two pumping cells 21 and 31 are electrically connected in parallel to each other in the present embodiment, the electrical connection can be simple and both cells can be controlled at the same time. Since both of the sensor cells 3 and 51 are also connected in parallel, their connection is simple and the sum of the ion current flowing through both sensor cells can be taken out easily. Since the sensor cells 3 and 51 are disposed at the downstream of the mixture diffusion, the NOx concentration can be measured after the oxygen contained in the gas mixture is sufficiently pumped out by the two pumping cells 21 and 31 disposed at the upstream of the mixture diffusion. Since the heater is disposed underneath the electrolyte layers, the pumping cells and the sensor cells can be quickly heated to a temperature at which they become active. Therefore, the NOx concentration is detected shortly after the engine is started, and accordingly the engine control and the deterioration detection of the three-way catalyzer can be done with a quick response.

The gas mixture inlet hole 121 is formed by a pin hole, and the oxygen outlet hole is formed by a small hole in the present embodiment. These inlet and outlet holes may be constituted by holes filled with a porous material therein.

Figure 8:
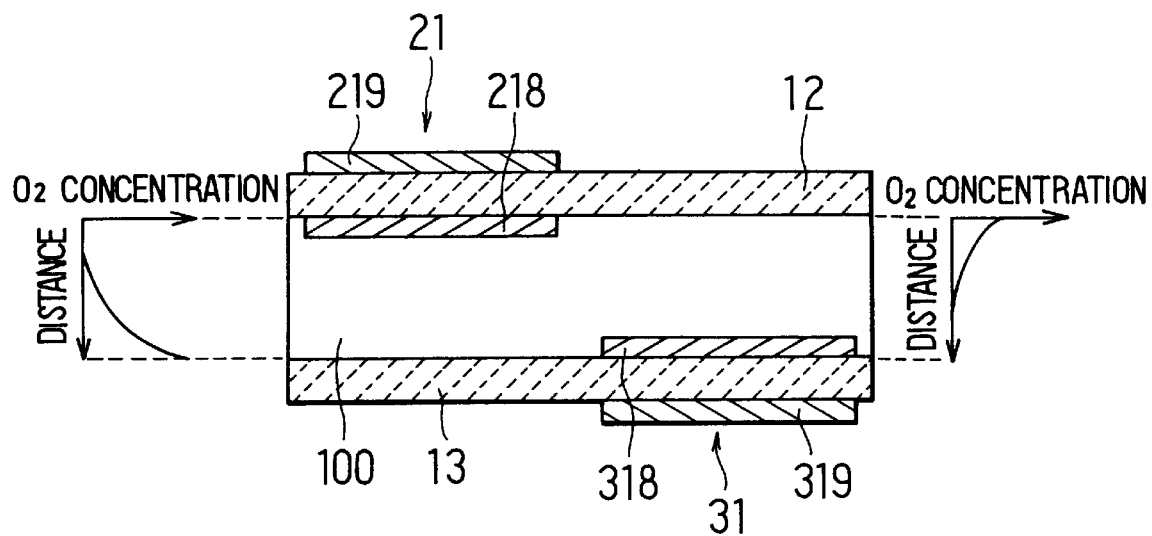
FIG. 8 is a cross-sectional view showing a possible modification of the first embodiment of the present invention.

The relative position of the first pumping cell 21 and the second pumping cell 31 may be modified as shown in FIG. 8. In FIG. 8, the second pumping cell 31 which is directly under the first pumping cell 21 in the embodiment shown in FIG. 2 is moved to the right side of the first pumping cell 21. In this structure, the oxygen in the gas mixture at the vicinity of the electrode 218 is pumped out by the first pumping cell 21 and the oxygen at the vicinity of the electrode 318 is pumped out by the second pumping cell 31. The oxygen concentration curves under the first pumping cell 21 and above the second pumping cell 31 become as illustrated by a left side graph and a right side graph in FIG. 8, respectively. The oxygen in the gas mixture chamber 100 can be pumped out to a substantially zero level (for example, lower than 0.01 ppm) as a whole in this structure, too.

(Second Embodiment)

Figure 9:
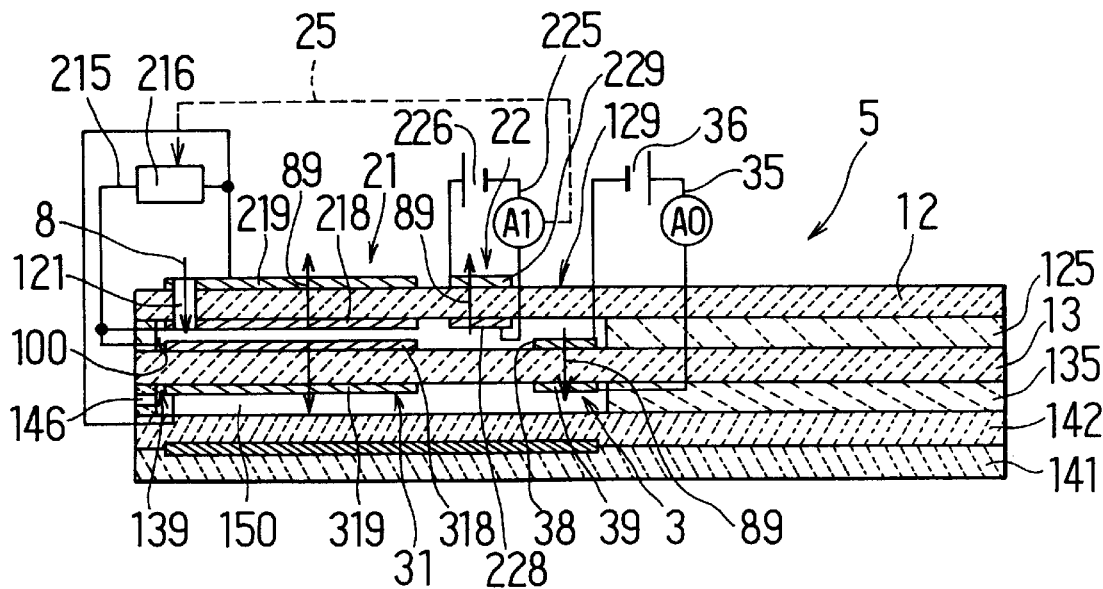
FIG. 9 is a cross-sectional view showing a gas sensor as a second embodiment according to the present invention.

Now, a second embodiment according to the present invention will be described, referring to FIGS. 9 through 11. The gas sensor 5 as the second embodiment shown in FIG. 9 has a similar structure as the first embodiment. Compared with the first embodiment, an oxygen sensor cell 22 is added between the pumping cells (21, 31) and the sensor cell, and only one sensor cell 3 is used in the second embodiment. Parts or components indicated by the same numerals as in the first embodiment perform the same functions as those of the first embodiment. Therefore, explanations for those are not repeated here, but explanations here will be focused on the differences.

The oxygen sensor cell 22 has a pair of electrodes 228 and 229 disposed on both surfaces of the first electrolyte 12. The electrode 228 faces the gas mixture in the gas mixture chamber 100 and is made of a platinum and gold alloy (Pt—Au) containing 1 weight-percent of gold which is inactive in reducing the oxygen of NOx into ions, and the other electrode 229 disposed on the outer surface 129 of the first electrolyte 12 is made of platinum (Pt). A constant voltage (for example, 0.8 V) is imposed between both electrodes 228 and 229 by a power source 226. The ion current proportional to oxygen gas concentration in the chamber 100 is measured by an ammeter A1 and is fed back to the circuit 215 via a controller 216 in order to keep the oxygen concentration in the chamber 100 at a constant level. The controller 216 includes a power source for applying a voltage to the pair of pumping cells 21 and 31 connected in parallel with each other and a variable resistance for controlling the voltage according to the ion current fed back from the oxygen sensor cell 22. The surface area of the electrodes 228 and 229 is about 12 mm$^2$ in this particular embodiment.

The gas sensor 5 as the second embodiment of the present invention operates in the following manner. The gas mixture in the exhaust pipe is introduced into the mixture chamber 100 through the inlet hole 121. The oxygen gas 89 contained in the gas mixture is pumped out by the oxygen pumping cells 21 and 31 in the same manner as in the first embodiment. The oxygen gas concentration in the chamber 100 is monitored by the oxygen sensor cell 22 which also operates as a pumping cell. The ion current flowing through the first electrolyte 12 represents the oxygen concentration in the chamber 100.

Figure 10:
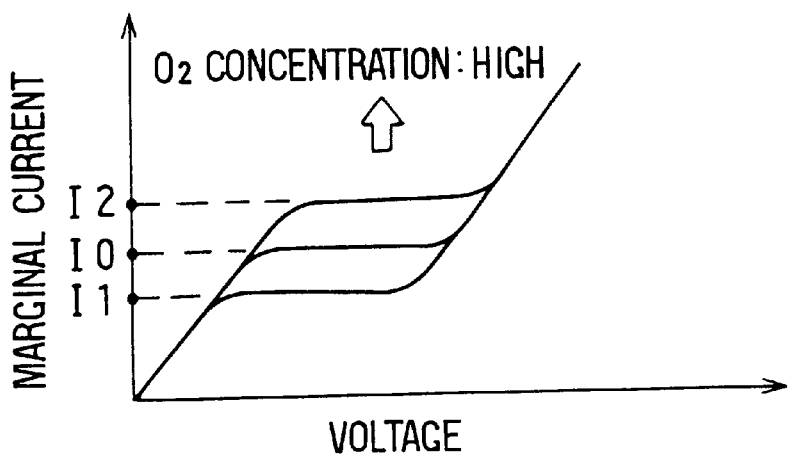
FIG. 10 is a graph showing a relation between a voltage supplied to an oxygen sensor cell of the second embodiment and its marginal current.

FIG. 10 shows a relation between the voltage imposed to the oxygen sensor cell 22 and a marginal ion current flowing therethrough. The marginal ion current means levels of the ion current which are flat irrespective of the voltage imposed. The larger the marginal current becomes, the higher the oxygen concentration in the chamber 100 is. In the graph of FIG. 10, the marginal current I0 corresponds to a target level of the oxygen concentration in the chamber 100, and the marginal current I2 and I1 correspond to a higher and a lower oxygen concentration, respectively. If the oxygen sensor cell 22 detects that the marginal current is I2, the voltage applied to the pumping cells 21 and 31 is increased so that the more oxygen is pumped out from the chamber 100. If the marginal current becomes I2, the voltage applied to the pumping cells 21 and 31 is decreased so that the pumping out of the oxygen is suppressed.

Figure 11:
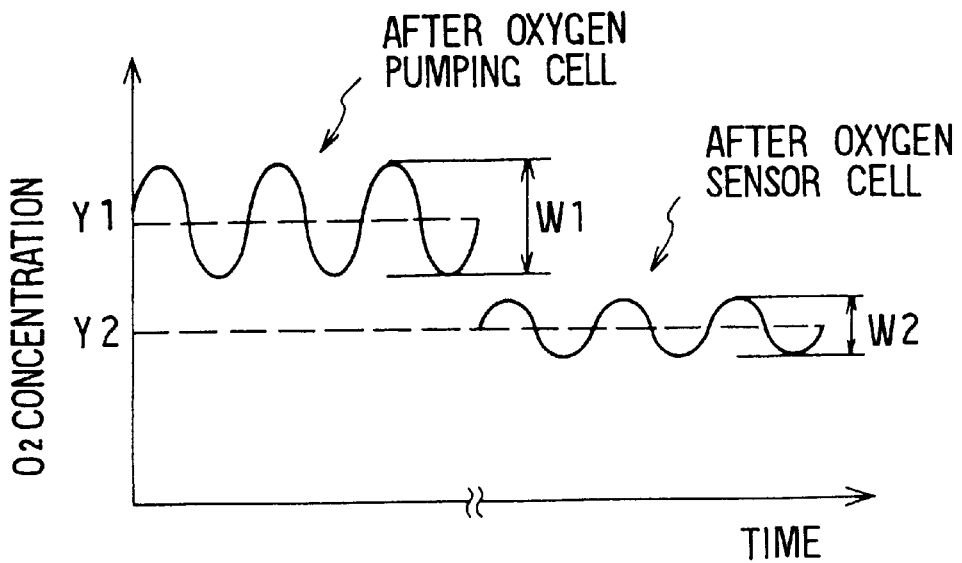
FIG. 11 is a graph showing the oxygen concentration in a gas mixture chamber of the second embodiment versus time.

By controlling the pumping out of the oxygen in the manner described above, the oxygen concentration around the pumping cell electrodes 218 and 318 in the chamber 100 becomes as shown in a upper graph in FIG. 11. The oxygen concentration fluctuates within a range of W1 which is sufficiently small for the purpose of keeping the level constant, and its average level is Y1. Since the oxygen gas is further pumped out by the oxygen sensor cell 22 in this embodiment, the oxygen concentration around the electrodes 228 and 229 of the sensor cell 22 becomes to a level shown in a lower graph in FIG. 11. It fluctuates within a smaller range W2 and its average level becomes Y2 which is lower than the level Y1. The gas mixture containing the very low level of oxygen reaches the electrode 38 of the sensor cell 3, where the oxygen of NOx is reduced into oxygen ions. The ammeter A0 connected to the sensor cell 3 detects the ion current proportional to the NOx concentration in the gas mixture in the same manner as in the first embodiment. Since the oxygen concentration in the gas mixture is kept at a substantially constant level, the NOx concentration in the gas mixture is accurately measured by the ammeter A0 without being interfered by the oxygen gas in the gas mixture.

Though the marginal ion current detected by the oxygen sensor cell 22 to which a constant voltage is imposed is used for controlling the pumping cells in the above embodiment, an voltage between the electrodes 38 and 39 of the oxygen cell 22 may be used for this purpose.

(Third Embodiment)

A gas sensor 6 as a third embodiment according to the present invention will be described, referring to FIGS. 12 through 15. Parts or components indicated by the same numerals as in the first and the second embodiments perform the same functions as in those embodiments and have similar structures. Therefore, detailed descriptions thereof are not repeated here, but differences of the third embodiment from the foregoing embodiments will be focused.

Figure 12:
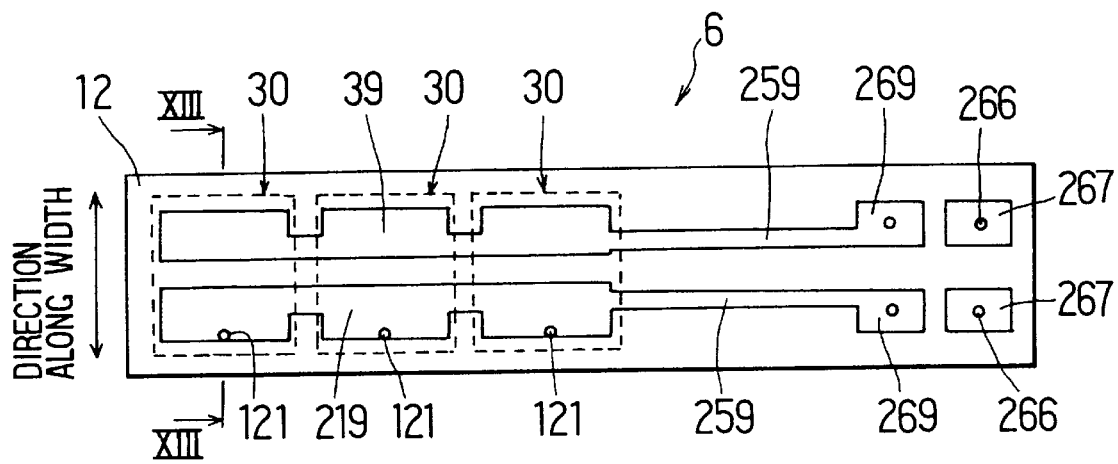
FIG. 12 is a top view showing a gas sensor as a third embodiment according to the present invention.
Figure 13:
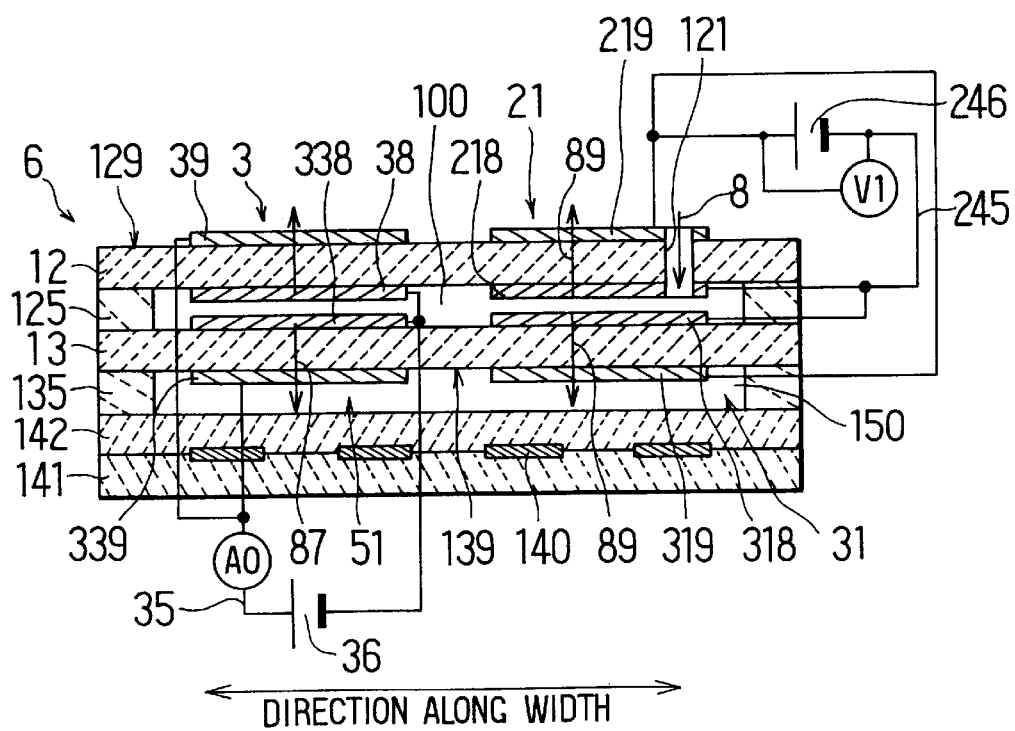
FIG. 13 is a cross-sectional view showing the second embodiment, taken along a line XIII—XIII of FIG. 12.
Figure 14:
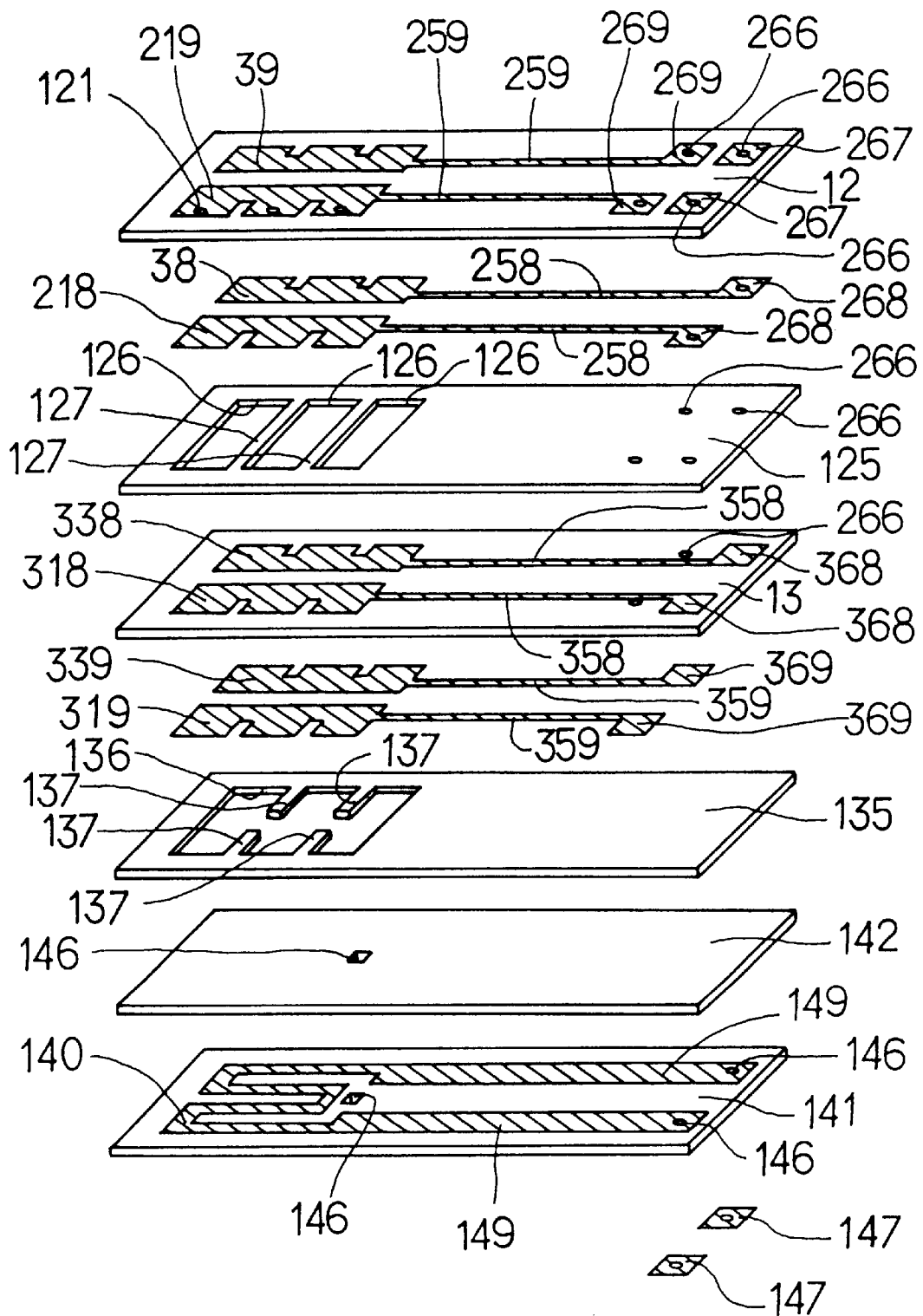
FIG. 14 is a perspective view showing each layer, separated from each other, used in the third embodiment.

In the third embodiment, the first pumping cell 21 and the first sensor cell 3 are disposed on the first solid electrolyte layer 12 next to each other in a direction along the width of the gas sensor 6 (as opposed to the foregoing embodiments in which those are disposed next to each other in a longitudinal direction of the gas sensor 1). In the same manner, the second pumping cell 31 and the second sensor cell 51 are disposed on the second solid electrolyte layer 13 next to each other in a direction along the width of the gas sensor 6. The pair of pumping cells 21 and 31 and the pair of sensor cells 3 and 51 constitute a unit 30, and three of the units 30 are disposed in series in the longitudinal direction of the sensor 6, as best seen in FIG. 12. The inlet hole for introducing the gas mixture into the chamber 100 is formed through the first pumping cell electrode 219 and the first electrolyte 12 of each unit 30, as shown in FIGS. 12, 13 and 14. As shown in FIG. 14, the gas mixture chamber 100 formed on the spacer layer 125 is divided by separating walls 127 into three chambers each facing each unit 30. The air passage 150 formed on the spacer layer 135 has three sections, partly separated with narrow walls 137, communicating with one another. Each surface area of the pumping cell electrodes 218, 219, 318 and 319 is about 40 mm$^2$ (in total of three units 30), and each surface area of the sensor electrodes 38, 39, 338 and 339 is about 30 mm$^2$ (in total of three units 30). The gas mixture inlet holes 121 are pin holes each having a diameter of 0.2 mm, and are formed at the edges of the pumping cell electrodes remotest from the sensor cell electrodes as best seen in FIG. 12. Other structures are the same or substantially the same as those of the first embodiment, and the gas sensor 6 is manufactured in the same processes as the first embodiment.

The present embodiment (the gas sensor 6) functions in the following manner. The gas sensor 6 is mounted in the exhaust pipe 50 as shown in FIG. 5, and the gas mixture (exhaust gas) is introduced into the mixture chamber 100 through the inlet holes 121 and diffuses in the chamber 100. The oxygen gas 89 contained in the gas mixture is pumped out by the pair of oxygen pumping cells 21 and 31 to which a constant voltage (for example, 0.8 V) is imposed. The oxygen concentration in the mixture gas is reduced to a substantially zero level (for example, lower than 0.01 ppm) by the pumping operation of the pumping cells. The gas mixture containing substantially no oxygen gas is diffused in the chamber 100 and contacts sensor electrodes 38 and 338. The oxygen of NOx in the gas mixture is reduced to oxygen ions 87 which are discharged from the chamber 100 by the pair of sensor cells 3 and 51 to which a constant voltage (for example, 0.5 V) is imposed. The ion current (the marginal current) proportional to the NOx concentration is measured by an ammeter A0 connected to the pair of sensor cells 3 and 51.

The diffusion passage in the chamber 100 from the pumping cells 21 and 31 to the sensor cells 3 and 51 is short in this embodiment because the pumping and sensor cells are disposed side by side in a direction along the width of the electrolyte layers 12 and 13, and the longitudinal length of both pumping and sensor cells can be made longer. In addition, since three units 30 each including the pumping and sensor cells are disposed in series in the longitudinal direction of the gas sensor 6 and the gas mixture is introduced into the chamber 100 from the three inlet holes 121 each disposed on the respective unit 30, an amount of gas mixture introduced from each inlet hole 121 can be made small. Accordingly, the oxygen contained in the gas mixture is sufficiently pumped out by each pair of pumping cells 21 and 31. This results in a higher sensitivity of the gas sensor 6.

Figure 15:
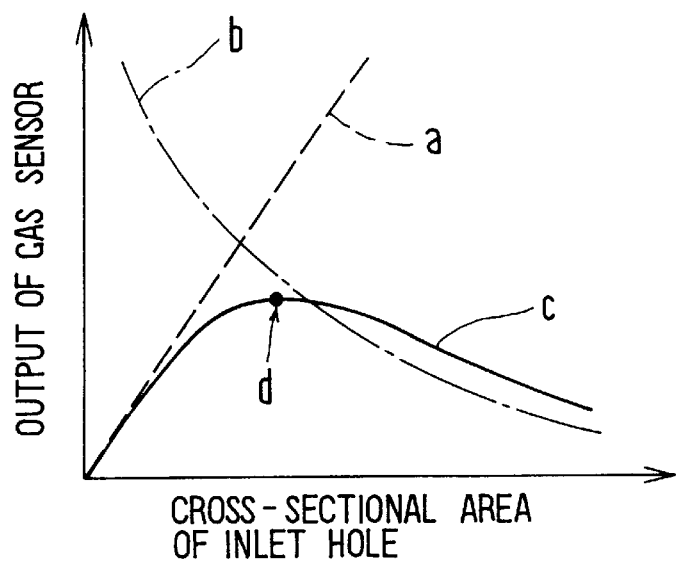
FIG. 15 is a graph showing a relation between a cross-sectional area of gas mixture inlet holes and an output of the gas sensor of the third embodiment.

FIG. 15 shows a relation between a cross-sectional area and an output of the gas sensor 6. If the surface area of the pumping cell electrode were very large and the diffusion distance from the pumping cell to the sensor cell were not considered, the output of the gas sensor would increase in proportion to the cross-sectional area of the inlet hole as shown in a line "a" of FIG. 15. On the other hand, the output of the gas sensor would decrease in proportion to the diffusion distance as shown in a curve "b" of FIG. 15, if the amount of the gas mixture introduced were constant. However, since the size of the pumping cell electrode has a certain limitation and the amount of the gas mixture increases according to an increase of the cross-sectional area of the inlet hole, the output of the gas sensor 6 becomes as shown in a curve "c" of FIG. 15. This means that there is an optimum size of the cross-sectional area of the inlet hole to obtain a maximum output from the gas sensor 6. A point "d" shows the maximum output. Therefore, it is preferable to select the size of inlet hole 121 at a size corresponding to the point "d".

Since the first sensor cell 3 and the second sensor cell 51 of each unit 30 are connected in parallel, the ion current proportional to the NOx concentration in the gas mixture is detected as a sum of two sensor cells, and, accordingly, the gas sensor 6 has a high sensitivity. Also, since the ion current is detected as a marginal current as described above, the gas sensor 6 shows a high sensitivity even to a small change of the NOx concentration. Since the gas mixture inlet holes 121 are formed at a remote end from the sensor cell, the oxygen contained in the gas mixture can be sufficiently pumped out by the pumping cells in the course of mixture gas diffusion in the chamber 100. Since the gas mixture chamber 100 is divided into three independent chambers each corresponding to each unit 30 as shown in FIG. 14, a substantially equal amount of the gas mixture diffuses to each pair of sensor cells 3 and 51. This contributes to obtaining a stable output from the gas sensor 6. Since the pumping out of the oxygen gas contained in the gas mixture is performed by the pair of oxygen pumping cells 21 and 31, the oxygen concentration in the chamber 100 can be lowered to the substantially zero level. Accordingly, the NOx concentration in the gas mixture can be detected with a high accuracy and a high sensitivity without being interfered by the oxygen gas contained in the gas mixture.

Figure 16:
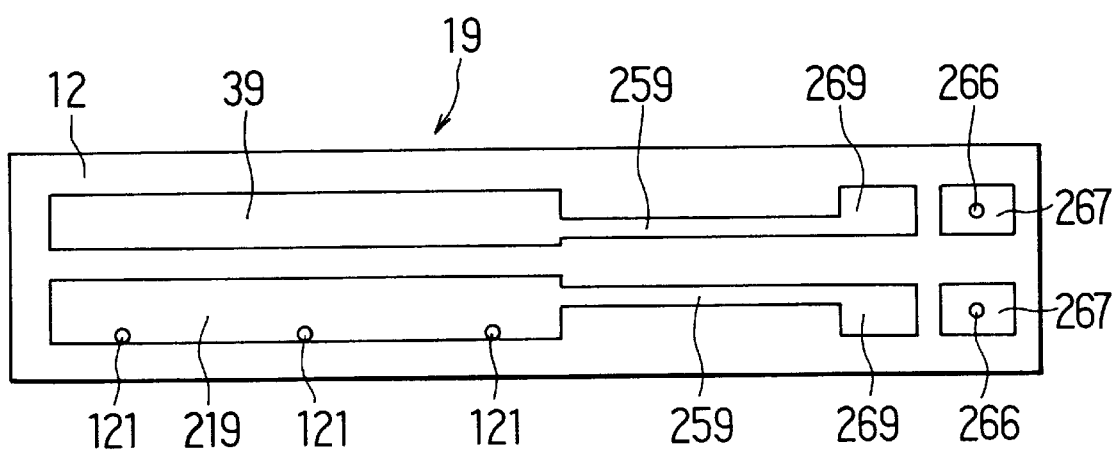
FIG. 16 is a top view showing a first modification of the third embodiment.

The gas sensor 6 described above as the third embodiment may be modified to a form shown in FIG. 16, in which the modified gas sensor is shown as a gas sensor 19. In this modification, all of the pumping cell electrodes and sensor cell electrodes composed of three parts in the third embodiment are unified in a single rectangular electrodes as shown in FIG. 16. Since the shape of electrode form is simplified in this modification, the gas sensor 19 can be manufactured in simpler processes.

Figure 17:
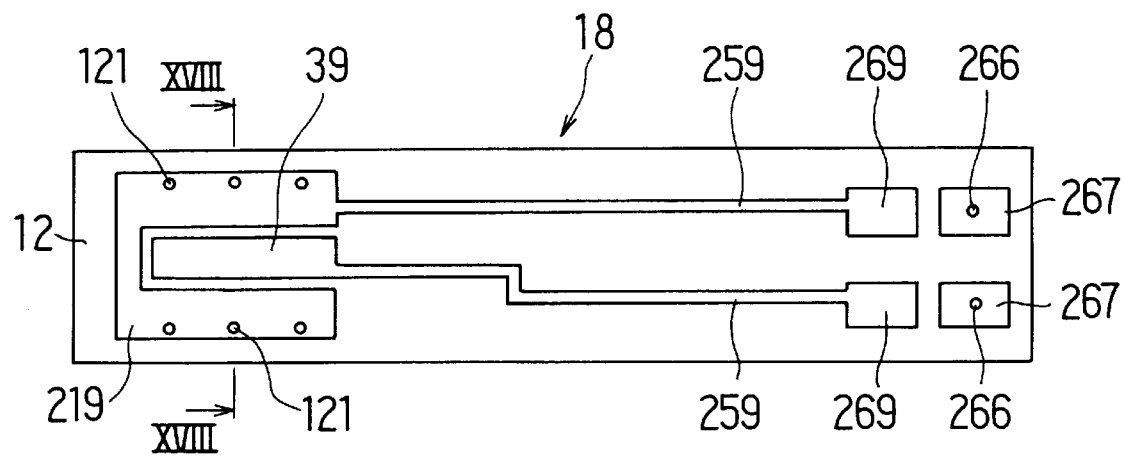
FIG. 17 is a top view showing a second modification of the third embodiment.
Figure 18:
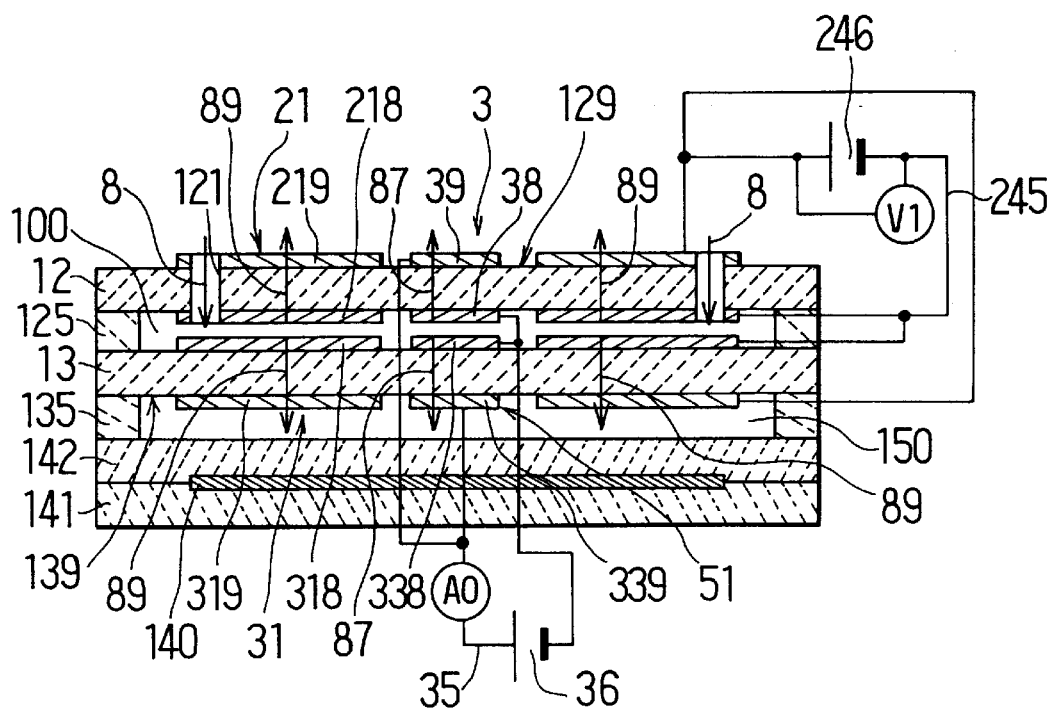
FIG. 18 is a cross-sectional view showing the second modification of the third embodiment, taken along a line XVIII—XVIII of FIG. 17.

It is also possible to modify the structure of the gas sensor 6 into a form shown in FIGS. 17 and 18, in which the modified gas sensor is shown as a gas sensor 18. In this modification, the first sensor cell 3 is disposed in a space formed in the first pumping cell 21, and the second sensor cell 51 is disposed in a space formed in the second pumping cell 31. In other words, the sensor electrode is located between the pumping electrodes, so that the gas diffusion distance from a pumping cell area to a sensor cell area in the chamber 100 becomes shorter. The gas mixture is introduced into the chamber 100 through six inlet holes 121 formed through first pumping cell electrodes (218, 219) and the first electrolyte layer 12. Other structures and functions of this modification are the same as those of the third embodiment. Since the diffusion distance is short in this modification, a larger amount of gas mixture can be diffused to the sensor cells, which in turn enhances the sensitivity of the gas sensor 18. Though the sensor cells are located between the pumping cells in this modification, the pumping cells may be located between the sensors cells. The same effect will be obtained in this structure, too.

(Fourth Embodiment)

Figure 19:
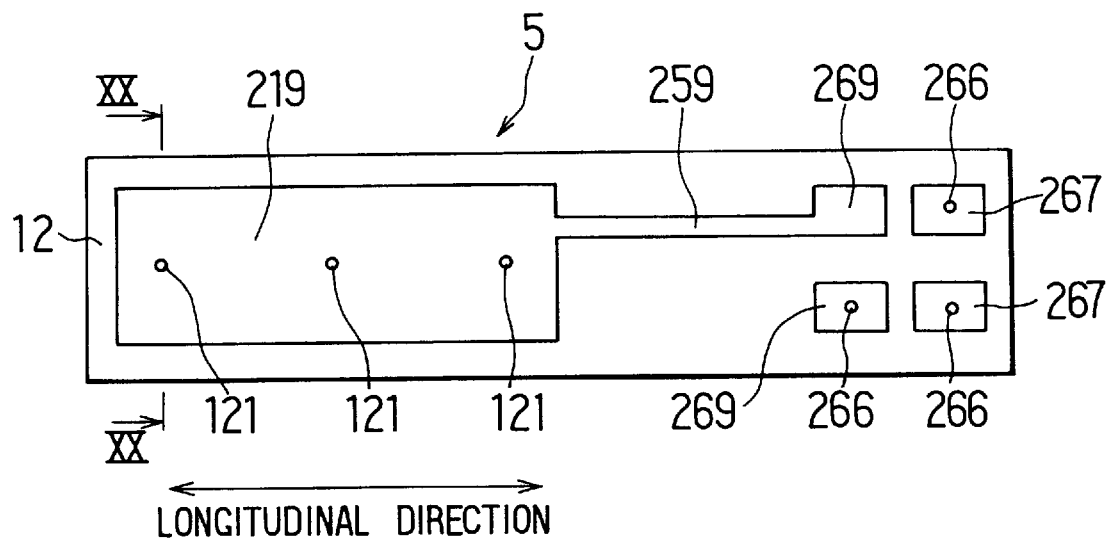
FIG. 19 is a top view showing a gas sensor as a fourth embodiment according to the present invention.
Figure 20:
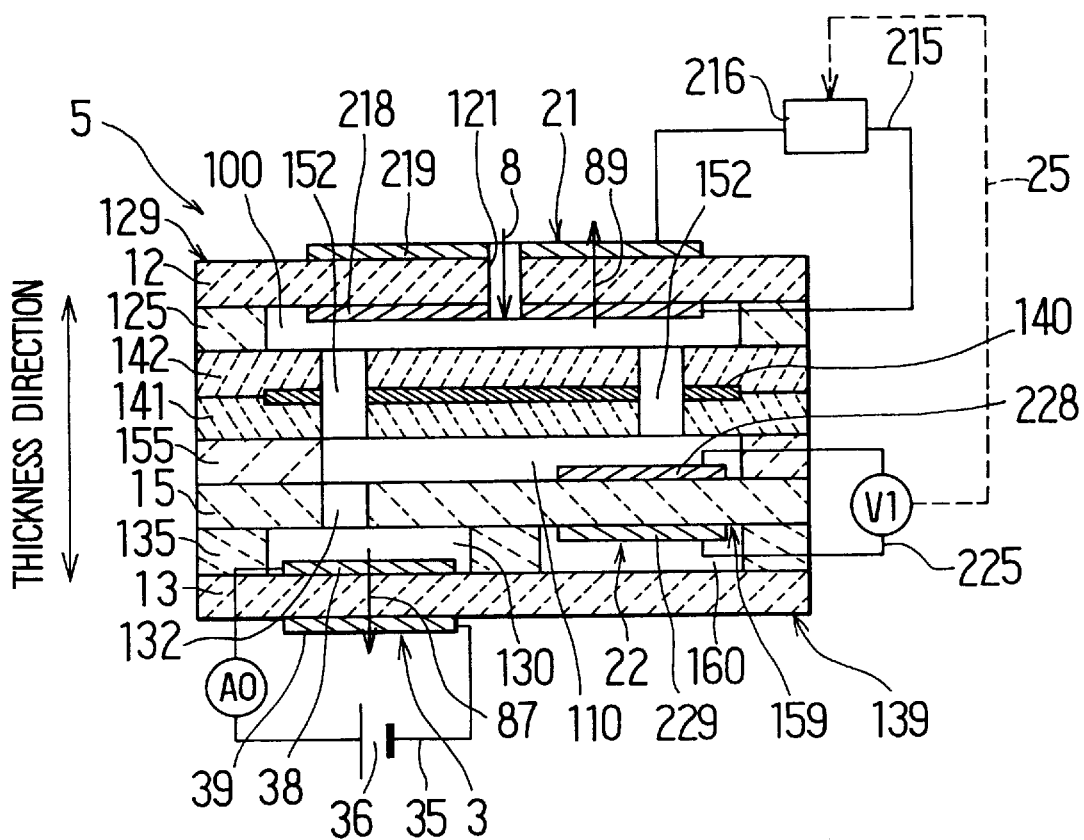
FIG. 20 is a cross-sectional view showing the fourth embodiment, taken along a line XX—XX of FIG. 19.

Referring to FIGS. 19 and 20, a fourth embodiment according to the present invention will be described. The gas sensor 5 of this embodiment is composed of an oxygen pumping cell 21, an oxygen sensor cell 22 and a sensor cell 3. As opposed to the foregoing embodiments described above, this embodiment uses only one oxygen pumping cell 21. Parts or components of this embodiment indicated by the same numerals as in the foregoing embodiments have the same or similar structures and perform the same or similar functions. Therefore, detailed descriptions for those parts or components will not be repeated, but structures and features peculiar to the present embodiment will be described hereafter.

As shown in FIG. 20, the oxygen pumping cell 21 is composed of an oxygen-ion-conductive solid electrolyte layer 12 and a pair of electrodes 218 and 219 disposed on both surfaces (an upper surface 129 and a lower surface) of the electrolyte 12. Underneath the pumping cell 21, a spacer layer 125 having a gas mixture chamber 100 formed thereon is disposed. A heater layer 141 having a heater film 140 printed thereon and a cover layer 142 covering the heater film 140 are disposed underneath the spacer layer 125. Underneath the heater layer 141, there is a spacer layer 155 having a sensor chamber 110 formed thereon. A oxygen sensor cell 22 composed of an oxygen-ion-conductive solid electrolyte layer 15 and a pair of electrodes 228 and 229 disposed on both surfaces (an upper surface and a lower surface 159) of the electrolyte layer 15 is disposed underneath the spacer layer 15. Then, comes a spacer layer 135 having a detection chamber 130 and an air chamber 160 both formed on the spacer layer 135. Underneath the spacer layer 135, there is a sensor cell 3 composed of an oxygen-ion-conductive solid electrolyte layer 13 and a pair of electrodes 38 and 39 disposed on both surfaces (an upper surface and a lower surface 139) of the electrolyte layer 13. All of these layers are laminated on one another in the order described above.

The gas mixture chamber 100 communicates with the inlet hole 121 through which the gas mixture is introduced. The gas mixture chamber 100 also communicates with the sensor chamber 110 through passages 152. The sensor chamber 110 communicates with the detection chamber 130 through a passage 132. Outside air is introduced into the air chamber 160. The passages 152 and 132 are formed not to directly communicate with the inlet hole 21, so that the oxygen contained in the gas mixture introduced into the chamber 100 is sufficiently pumped out by the oxygen sensor cell 21 before the gas mixture in the chamber 100 diffuses into the sensor chamber 110 and the detection chamber 130. One of the pumping cell electrodes 218 is exposed to the gas mixture in the chamber 100, and one of the sensor cell electrodes 38 is exposed to the gas mixture in the detection chamber 130. One electrode 228 of the oxygen sensor cell 22 is exposed to the gas mixture in the sensor chamber 110 and the other electrode 229 to the air in the air chamber 160.

A voltmeter V1 is connected between oxygen sensor cell electrodes 228 and 229 through a circuit 225 to measure the voltage between both electrodes. A controller 216 is connected between the pumping cell electrodes 218 and 219 through a circuit 215 to control a voltage to be supplied to the pumping cell 21 according to the voltage V1 sensed by the oxygen sensor cell 22 which is fed back to the controller 216 through a feed back circuit 25. A constant voltage (for example, 0.5 V) is imposed on the sensor cell 3 by a power source 36 through a circuit 35. An ammeter A0 is disposed in the circuit 35 to measure the ion current flowing through the sensor cell 3.

The pumping cell electrode 218 exposed to the gas mixture in the chamber 100 and the oxygen sensor cell electrode 228 exposed to the gas mixture in the sensor chamber 110 are made of a material, such as a platinum and gold alloy (Pt—Au) containing one weight percent of gold, which is inactive in reducing the oxygen of NOx into oxygen ions. All other electrodes 38, 39, 219 and 229 are made of platinum (Pt). The surface area of the pumping cell electrodes 218 and 219 is about 70 mm$^2$, that of the sensor cell electrodes 38 and 39 is about 40 mm$^2$, and that of the oxygen sensor cell electrodes 228 and 229 is about 30 mm$^2$, in this particular embodiment. The thickness of each layer is about 0.16 mm, and the diffusion distance from the pumping cell 21 to the sensor cell 3 (a total thickness of six layers 125, 142, 141, 155, 15 and 135) is about 0.96 mm.

The NOx concentration in the gas mixture which is the exhaust gas from an internal combustion engine is sensed by the gas sensor 5 (the fourth embodiment) in the following manner. The gas mixture 8 is introduced into the mixture chamber 100 through the inlet hole 121. The oxygen gas 89 contained in the gas mixture is pumped out by the operation of the pumping cell 21. Then, the gas mixture diffuses to the sensor chamber 110 through the passages 152, and the oxygen concentration of the gas mixture in the sensor chamber 110 is monitored by the oxygen sensor cell 22. The voltage V1 detected by the oxygen sensor cell 22 corresponds to the oxygen concentration difference between the sensor chamber 110 and the air chamber 160. The voltage V1 is fed back to the controller 216 through the feedback circuit 25. The controller 216 controls the voltage supplied to the pumping cell 21, so that the oxygen concentration in the chamber 100 becomes a very low and constant level. In case the oxygen concentration in the sensor chamber 110 is higher than a predetermined target level, the voltage V1 becomes lower than a standard value, and the controller 216 increases the voltage to be supplied to the pumping cell 21, responding to the voltage V1 fed back from the oxygen sensor cell 22, to increase the amount of the oxygen pumped out by the pumping cell 21. In case the oxygen concentration in the sensor chamber 110 is low, the voltage V1 becomes high, and the supply voltage to the pumping cell 21 is decreased by the controller 216 thereby to decrease the amount of oxygen pumped out from the chamber 100. Thus, the oxygen concentration is kept at a constant and substantially zero level (for example, 0.0001 ppm).

The gas mixture containing substantially no oxygen diffuses into the detection chamber 130 through the passages 152 and 132. The oxygen of the NOx contained in the gas mixture is reduced to oxygen ions by the sensor cell 3, and discharged to the outside through the electrolyte layer 13, thereby generating the ion current which is proportional to the NOx concentration in the gas mixture. The ion current (marginal current) is measured by the ammeter A0.

Since the sensor cell 22 is disposed directly under the pumping cell 21, the diffusion distance of the gas mixture can be made short (0.96 mm in this particular embodiment as mentioned above). The oxygen gas contained in the gas mixture is almost perfectly pumped out by the pumping cell 21, and, then, the gas mixture diffuses to the sensor cell 3 with the short diffusion distance. Therefore, the NOx concentration in the gas mixture is measured by the sensor cell 3 with a high accuracy and a high sensitivity. Since the pumping cell 21, the oxygen sensor cell 22 and the sensor cell 3 are disposed separately and independently form one another, the interference among the signals of these cells can be surely suppressed.

Though the voltage V1 generated in the oxygen sensor cell 22 is used as a signal to control the supply voltage to the pumping cell 21 in this embodiment, a marginal ion current of the oxygen sensor cell 22 which is obtained by applying a constant voltage to the oxygen sensor cell 22 may be used as the control signal.

While the present invention has been shown and described with reference to the foregoing preferred embodiments, it will be apparent to those skilled in the art that changes in form and detail may be made therein without departing from the scope of the invention as defined in the appended claims.

What is claimed is:

1. A solid electrolyte gas sensor for measuring a concentration of a constituent gas in a gas mixture, the gas sensor comprising:

a gas mixture chamber;

a gas mixture inlet hole through which the gas mixture is introduced into the gas mixture chamber;

a first oxygen pumping cell composed of a first oxygen-ion-conductive solid electrolyte layer and a pair of electrodes disposed on both surfaces of the first electrolyte layer, one of the electrodes being exposed to the gas mixture in the gas mixture chamber;

a second oxygen pumping cell composed of a second oxygen-ion-conductive solid electrolyte layer and a pair of electrodes disposed on both surfaces of the second electrolyte layer, one of the electrodes being exposed to the gas mixture in the gas mixture chamber;

said first and second electrolyte layers being laminated on each other, so that the gas mixture chamber is formed therebetween, said first and second oxygen pumping cells are electrically insulated from each other, and said first and second oxygen pumping cells are disposed in at least partially overlapped facing relation to each other, each facing the gas mixture chamber; and at least one sensor cell having a pair of electrodes disposed on both surfaces of either one of the electrolyte layers, one of said electrodes of said sensor cell being exposed to the gas mixture in the gas mixture chamber, wherein:

both said oxygen pumping cells are disposed upstream of the at least one sensor cell with respect to a direction of flow of the (as mixture in the gas mixture chamber;

oxygen gas contained in the gas mixture introduced into the gas mixture chamber is pumped out therefrom by the first and the second oxygen pumping cells so that the oxygen gas concentration is reduced to substantially zero; and a concentration of the constituent gas in the gas mixture in the gas mixture chamber is measured by the sensor cell.

2. A solid electrolyte gas sensor according to claim 1, wherein the gas sensor includes: a first sensor cell having a pair of electrodes disposed on both surfaces of the first electrolyte layer, one of the electrodes being exposed to the gas mixture in the gas mixture chamber; and a second sensor cell having a pair of electrodes disposed on both surfaces of the second electrolyte layer, one of the electrodes being exposed to the gas mixture in the gas mixture chamber.

3. A solid electrolyte gas sensor according to claim 2, the first and the second sensor cells are connected electrically in parallel to each other.

4. A solid electrolyte gas sensor according to claim 1, wherein the both electrolyte layers are formed in a rectangular shape having short sides and long sides.

5. A solid electrolyte gas sensor according to claim 4, wherein one of the oxygen pumping cells and the sensor cell are aligned side by side in a direction along the long side of the electrolyte layer, so that the gas mixture introduced into the gas mixture chamber diffuses from the oxygen pumping cells to the sensor cell.

6. A solid electrolyte gas sensor according to claim 4, wherein one of the oxygen pumping cells and the sensor cell are aligned side by side in a direction along the short side of the electrolyte layer, so that the gas mixture introduced into the gas mixture chamber diffuses from the oxygen pumping cells to the sensor cell.

7. A solid electrolyte gas sensor according to claim 6, wherein the oxygen pumping cells and the sensor cell are elongated in the direction along the long side of the electrolyte layer and a plurality of the gas mixture inlet holes are formed through the first oxygen pumping cell.

8. A solid electrolyte gas sensor according to claim 7, wherein the gas mixture chamber is divided into a plurality of chambers each corresponding to each of the gas mixture inlet holes.

9. A solid electrolyte gas sensor according to claim 7, wherein the gas mixture inlet holes are formed at positions most remote from the at least one sensor cell.

10. A solid electrolyte gas sensor according to claim 4, wherein the sensor cell electrodes are placed so that the sensor cell electrodes are surrounded by the oxygen pumping cell electrodes disposed on said one of said electrolyte layers.

11. A solid electrolyte gas sensor according to claim 4, wherein said sensor cell electrodes are disposed on said first electrolyte layer and the electrodes of said first oxygen pumping cell are placed so that the oxygen pumping cell electrodes are surrounded by the sensor cell electrodes.

12. A solid electrolyte gas sensor according to claim 1, further comprising an oxygen sensor cell, disposed between the oxygen pumping cells and the sensor cell, for detecting oxygen concentration in the gas mixture after the oxygen contained in the gas mixture is pumped out by the oxygen pumping cells and for feeding back a signal corresponding to the detected oxygen concentration to the oxygen pumping cells to maintain the oxygen concentration in the mixture chamber at a constant level.

13. A solid electrolyte gas sensor according to claim 1, wherein the first and the second oxygen pumping cells are connected electrically in parallel to each other.

14. A solid gas electrolyte gas sensor according to claim 13, wherein a constant voltage is imposed between the electrodes of the first oxygen pumping cell and a constant voltage is imposed between the electrodes of the second oxygen pumping cell.

15. A solid gas electrolyte gas sensor according to claim 14, wherein the constant voltage imposed between the electrodes of the first oxygen pumping cell is equal to the constant voltage imposed between the electrodes of the second oxygen pumping cell.

16. A solid electrolyte gas sensor according to claim 1, wherein the concentration of the constituent gas in the gas mixture is measured based on a marginal current generated in the sensor cell by supplying a constant voltage to the sensor cell.

17. A solid electrolyte gas sensor according to claim 1, wherein the constituent gas the concentration of which is me assured by the gas sensor is nitrogen-oxides (NOx).

18. A solid gas electrolyte gas sensor according to claim 1, wherein said one electrode of said first oxygen pumping cell and said one electrode of said second oxygen pumping cell are disposed in at least partially overlapped, facing relation to each other.

19. A solid gas electrolyte gas sensor according to claim 18, wherein said one electrode of said first oxygen pumping cell and said one electrode of said second oxygen pumping cell are substantially coextensive so as to be disposed in fully overlapped relation to each other, facing the gas mixture chamber.

20. A solid gas electrolyte gas sensor according to claim 1, wherein a constant voltage is imposed between the electrodes of the first oxygen pumping cell and a constant voltage is imposed between the electrodes of the second oxygen pumping cell.

21. A solid gas electrolyte gas sensor according to claim 20, wherein the constant voltage imposed between the electrodes of the first oxygen pumping cell is equal to the constant voltage imposed between the electrodes of the second oxygen pumping cell.

22. A solid gas electrolyte gas sensor according to claim 21, wherein the one electrode of said first oxygen pumping cell and the one electrode of the second oxygen pumping cell, each of which is exposed to the gas mixture in the gas mixture chamber, are made of a material which is inactive with said constituent gas, and said one electrode of at least one sensor cell exposed to the gas mixture in the gas mixture chamber is made of a material which is reactive with said constituent gas, whereby said first and second oxygen pumping cells selectively pump out substantially only oxygen in the gas mixture and the sensor cell measures a concentration of oxygen ions generated by reduction of the constituent gas by said reactive electrode of the sensor cell, whereby a concentration of the constituent gas is measured.

23. A solid gas electrolyte gas sensor according to claim 20, wherein the one electrode of said first oxygen pumping cell and the one electrode of the second oxygen pumping cell, each of which is exposed to the gas mixture in the gas mixture chamber, are made of a material which is inactive with said constituent gas, and said one electrode of at least one sensor cell exposed to the gas mixture in the gas mixture chamber is made of a material which is reactive with said constituent gas, whereby said first and second oxygen pumping cells selectively pump out substantially only oxygen in the gas mixture and the sensor cell measures a concentration of oxygen ions generated by reduction of the constituent gas by said reactive electrode of the sensor cell, whereby a concentration of the constituent gas is measured.

24. A solid gas electrolyte gas sensor according to claim 23, wherein the gas mixture in the gas mixture chamber includes oxygen and nitrogen-oxides (NOx).

25. A solid gas electrolyte gas sensor according to claim 24, wherein a constant voltage power source is connected to said pair of electrodes of said sensor cell whereby oxygen ions are pumped out from the gas mixture chamber by imposing a constant voltage from said constant voltage power source on said electrodes of the sensor cell and further comprising an ammeter connected to said sensor cell for measuring current generated by said pumping out said oxygen ions, whereby a concentration of said constituent gas in said gas mixture can be measured.

26. A solid gas electrolyte gas sensor according to claim 25, wherein said one electrode of said first oxygen pumping cell and said one electrode of said second oxygen pumping cell are substantially coextensive so as to be disposed in fully overlapped relation with each other, facing the gas mixture chamber.

27. A solid electrolyte gas sensor for measuring a concentration of a constituent gas in a gas mixture, the gas sensor comprising;

an inner cavity;

an inlet passage through which the gas mixture is introduced into the inner cavity;

a first oxygen ion conductive solid electrolyte layer having a pair of electrodes disposed on both surfaces thereof, one of the electrodes being exposed to the gas mixture in the inner cavity, the first electrolyte layer and the pair of electrodes constituting a first oxygen pumping cell;

a spacer layer which has at least a portion of the inner cavity formed therein laminated on the first solid electrolyte;

a second oxygen ion conductive solid electrolyte layer having a pair of electrodes disposed on both surfaces thereof, one of said electrodes being exposed to the gas mixture in the inner cavity, the second electrolyte layer and the pair of electrodes constituting a second oxygen pumping cell, the second electrolyte layer being laminated with the first electrolyte layer with the spacer layer interposed therebetween, so that the inner cavity is formed between said first and second electrolyte layers, said first and second oxygen pumping cells are electrically insulated from each other, and said first and second oxygen pumping cells are disposed in at least partially overlapped, facing relation to each other, each facing the inner cavity; and a pair of sensor cell electrodes respectively disposed on both surfaces of one of said electrolyte layers, one of said sensor cell electrodes being exposed to the gas mixture in the inner cavity, said one of said electrolyte layers and the pair of sensor cell electrodes constituting a sensor cell, wherein:

both said oxygen pumping cells are disposed upstream of the sensor cell with respect to a direction of flow of the gas mixture in the inner cavity;

oxygen gas contained in the gas mixture introduced into the inner cavity is pumped out therefrom by the first and the second oxygen pumping cells so that the oxygen gas concentration is reduced to substantially zero; and a concentration of the constituent gas in the gas mixture in the inner cavity is measured by the sensor cell.

28. A solid electrolyte gas sensor as in claim 27, wherein said one electrode of said first oxygen pumping cell and said one electrode of said second oxygen pumping cell are in substantially completely overlapped, facing relation to each other.

29. A solid electrolyte gas sensor as in claim 27, wherein the one electrode of said first oxygen pumping cell and the one electrode of the second oxygen pumping cell, each of which is exposed to the gas mixture in the inner cavity, are made of a material which is inactive with said constituent gas, said one electrode of the sensor cell exposed to the gas mixture in the inner cavity being made of a material which is reactive with said constituent gas, whereby said first and second oxygen pumping cells selectively pump out substantially only oxygen in the gas mixture and the sensor cell measures a concentration of oxygen ions generated by reduction of the constituent gas by said reactive electrode of said sensor cell, whereby a concentration of the constituent gas is measured.

* * * * *

UNITED STATES PATENT AND TRADEMARK OFFICE

CERTIFICATE OF CORRECTION

PATENT NO. : 6,068,747
DATED : May 30, 2000
INVENTOR(S) : TOJO et al

It is certified that error appears in the above-identified patent and that said letters patent is hereby corrected as shown below:

On the Title Page, column 1, Item [56]   References Cited the following citations should be added:

Under the Heading U.S. PATENT DOCUMENTS

--5,034,112......07/1991

5,304,294......04/1994

5,985,118......11/1999--

Under the Heading FOREIGN PATENT DOCUMENTS

--2,288,873   11/1995   United Kingdom--

Signed and Sealed this

Third Day of April, 2001

*Attest:*

NICHOLAS P. GODICI

*Attesting Officer*   *Acting Director of the United States Patent and Trademark Office*